(12) United States Patent
Willcock

(10) Patent No.: US 8,650,141 B2
(45) Date of Patent: Feb. 11, 2014

(54) SYSTEM AND METHOD OF SEGMENTING AND TAGGING ENTITIES BASED ON PROFILE MATCHING USING A MULTI-MEDIA SURVEY

(75) Inventor: Alex Willcock, Balcombe (GB)

(73) Assignee: Imagini Holdings Limited, London (GB)

( * ) Notice: Subject to any disclaimer, the term of this patent is extended or adjusted under 35 U.S.C. 154(b) by 1106 days.

(21) Appl. No.: 12/294,934

(22) PCT Filed: Mar. 27, 2007

(86) PCT No.: PCT/US2007/064970
§ 371 (c)(1),
(2), (4) Date: Sep. 28, 2008

(87) PCT Pub. No.: WO2007/117979
PCT Pub. Date: Oct. 18, 2007

(65) Prior Publication Data
US 2010/0179950 A1    Jul. 15, 2010

Related U.S. Application Data

(60) Provisional application No. 60/787,546, filed on Mar. 31, 2006.

(51) Int. Cl.
*G06N 5/00*    (2006.01)
(52) U.S. Cl.
USPC ............................. 706/45; 713/186; 705/7.32
(58) Field of Classification Search
USPC ....................... 706/45, 16; 713/186; 705/7.32
See application file for complete search history.

(56) References Cited

U.S. PATENT DOCUMENTS

| | | | |
|---|---|---|---|
| 4,945,478 A |  | 7/1990 | Merickel et al. |
| 5,219,433 A | * | 6/1993 | Zaruba et al. ................. 273/432 |
| 5,668,965 A |  | 9/1997 | Furusawa et al. |
| 5,754,939 A |  | 5/1998 | Eisner et al. |
| 6,029,195 A | * | 2/2000 | Herz ............................. 725/116 |
| 6,189,029 B1 |  | 2/2001 | Fuerst |
| 6,219,657 B1 |  | 4/2001 | Hatayama |
| 6,658,391 B1 |  | 12/2003 | Williams et al. |

(Continued)

FOREIGN PATENT DOCUMENTS

| | | |
|---|---|---|
| WO | WO99/60503 | 11/1999 |
| WO | WO01/06441 | 1/2001 |

OTHER PUBLICATIONS

"Ubiquitous advertising on the WWW: Merging advertisement on the browser", Youji Kohda, Susumu Endo, Computer Networks and ISDN Systems, vol. 28, Issues 7-11, May 1996, pp. 1493-1499.*

(Continued)

*Primary Examiner* — Kakali Chaki
*Assistant Examiner* — Mai T Tran
(74) *Attorney, Agent, or Firm* — Eagle IP Limited; Jacqueline C. Lui

(57) ABSTRACT

A system and method of profile matching using a multi-media survey is described. The method is capable to capturing the emotional reflex of a user. The method is generalized to categorizing an entity (a user or an object) to specific segment with similar emotional profiles. Each entity can be assigned to an emotional code. Such code can be used as a universal vocabulary in the emotional space for both commerce and consumers to adopt in facilitating communication among different parties.

21 Claims, 14 Drawing Sheets

(56) References Cited

U.S. PATENT DOCUMENTS

| | | |
|---|---|---|
| 6,826,540 B1 | 11/2004 | Plantec et al. |
| 7,228,283 B1 | 6/2007 | Hornstein |
| 7,739,140 B2 | 6/2010 | Vinson et al. |
| 8,200,504 B2 | 6/2012 | Williams et al. |
| 2001/0007100 A1 | 7/2001 | Revashetti et al. |
| 2002/0016731 A1 | 2/2002 | Kupersmit |
| 2002/0052774 A1 | 5/2002 | Alvarez et al. |
| 2002/0103786 A1 | 8/2002 | Goel |
| 2002/0152110 A1 | 10/2002 | Bennett et al. |
| 2003/0046140 A1 | 3/2003 | Callahan |
| 2003/0063779 A1 | 4/2003 | Wrigley |
| 2004/0101212 A1 | 5/2004 | Endrikhovski et al. |
| 2004/0210661 A1 | 10/2004 | Thompson |
| 2004/0230989 A1 | 11/2004 | Erickson et al. |
| 2005/0079474 A1 | 4/2005 | Lowe |
| 2005/0223237 A1 | 10/2005 | Barletta et al. |
| 2005/0234972 A1 | 10/2005 | Zeng et al. |
| 2005/0253554 A1* | 11/2005 | DiFazio et al. .............. 320/114 |
| 2007/0067273 A1 | 3/2007 | Willcock |

OTHER PUBLICATIONS

Nicu Sebe et al, 'Multimodal Emotion Recognition', Jun. 18, 2004, Handbook of Pattern Recognition and Computer Vision, pp. 1-23.

Oge Marques et al, 'Content-Based Visual Information Retrieval', Florida Atlantic University, USA, Jan. 31, 2002 Distributed multimedia databases: Techniques and applications, pp. 37-58.

Youji Kohda and Susumu Endo, "Ubiquitous Advertising on the WWW: Merging Advertisement on the Browser," Computer Networks and ISDN Systems, May 1996, pp. 1493-1499, vol. 28, issues 11.

* cited by examiner

SYSTEM AND METHOD OF SEGMENTING AND TAGGING ENTITIES BASED ON PROFILE MATCHING USING A MULTI-MEDIA SURVEY

RELATED APPLICATIONS

This patent application is a National Stage of International Application Serial No. PCT/US2007/064970, filed Mar. 27, 2007, which claims the benefit of U.S. Provisional Application Ser. No. 60/787,546, filed on Mar. 31, 2006, the disclosures of which are all incorporated herein by reference in their entireties.

FIELD OF INVENTION

This invention relates to a computerized system that performs emotional profile clustering, segmenting user groups, and assigning emotional codes to entities based on the clustering result.

BACKGROUND OF INVENTION

Conventional text-based survey has been practiced for many years in an attempt to understand user preferences. Typically, such survey consists of a question and multiple answers all written in text form. This kind of surveys is effective only in gathering the demographic and factual information from users. Since it requires users to exercise his logical thought process to answer questions, it is not effective in capturing users' emotional reflex. However, it is well observed that humans make snap judgments based on instinctive emotional inclination. As a result, there is a severe limitation in using conventional text-based survey to understand the emotional preferences of users. As a result, marketing campaign based on demographic survey alone may not be very effective.

SUMMARY OF INVENTION

In the light of the foregoing background, it is an object of the present invention to provide an alternative survey method that can capture the emotional reflex of users and segment those users with similar emotional preferences to the same category. Once done, the individual user can be tagged with an emotional code pin-pointing his emotional category and this code can be used in many commerce applications to enhance their search and match capabilities.

Accordingly, the present invention, in one aspect, provides a method for emotional profiling by first conducting an emotional survey to a user group. This survey comprises at least one survey form; and each form comprises a question and a plurality of multi-media objects for the users to choose from. The multi-media objects can be but not limited to images, photographs, video clips, audio files, or any combination thereof. This survey is intended to capture the emotional reflex of the users. Once a set of survey results are obtained, cluster analysis can be performed to segregate the users into at least one cluster. Each cluster represents a user segment with similar emotional preferences, and an emotional code can be assigned to this cluster.

In a preferred embodiment, each user is assigned an emotional code of the cluster to which this user belongs. This becomes his personal emotional code and is also referred as his emotional fingerprint or emotional DNA.

In yet another preferred embodiment, an object can also be assigned to an emotional code. This can be done by firstly assembling a user community; obtaining the personal emotional code of each the user in the user community; adding the number of users in the user community belonging to that personal emotional code; identifying the personal emotional code that has the highest number of users; and assigning the personal emotional code as the object emotional code of that object.

In a variation of the above method, this invention further comprises the steps of refining the emotional preferences to finer details. This is done by (a) identifying one user segment; (b) performing a second cluster analysis on that user segment to obtain at least one sub-cluster; and (c) assigning a sub-emotional code to the sub-cluster. This procedure can be recursively applied so that sub-sub-emotional code for sub-sub-clusters can be created.

In a further aspect of the present invention, there is further provided a method of matching the emotional code of one entity against another. An entity is defined here as either a human person or an object. An object can be but not limited to a company, a product, a service or a brand. The personal emotional code of a user and object emotional code of an object can be used to compare against each other to arrive at a matching score. The matching score indicates the emotional similarity of the two entities and this will facilitate many existing search and match applications.

In another aspect of this invention, a computerized emotional profiling system is provided to implement the aforementioned inventive methods.

In one embodiment, the system is configured to communicate with the user via a desk-top computer, a portable computer, an information kiosk, a wireless mobile phone device, an interactive TV or an Internet TV.

In yet another embodiment of the present invention, the personal emotional code can be stored in a non-volatile storage device under the specific user's possession. This device can be a credit card, a debit card, a smart card, an identity card, a Subscriber Identification Module (SIM) card, or a Universal Subscriber Identification Module (USIM) card.

There are many advantages to the present invention. One advantage is that it can capture the emotional reflex of a user, something that cannot be done by conventional text-based questionnaires. It is well known in the art that consumers make snap judgment decision in their buying habits. Such decision is largely based on their instinctive emotional preferences rather than a logical, analytical thought process. The emotional profiling methodology therefore provides additional insight for market researchers to understand the behavior of the consumers. Such insights cannot be obtained by conventional text-based surveys.

Another advantage of the present invention is that when all users and objects are tagged with their respectively emotional code, it allows market researchers to perform targeted marketing in the emotional space. The emotional code can become a universally accepted vocabulary of communication in that space so that commerce can zoom into what the consumer actually likes immediately. Similarly, users can also find like-minded users easily.

DETAILED DESCRIPTION OF THE PREFERRED EMBODIMENTS

As used herein and in the claims, "comprising" means including the following elements but not excluding others. Moreover, "entity" includes both a living being such as a user, and an object. The term "object" is used herewith to denote a non-living entity such as but not limited to a company, a corporation, a product, a service, or a brand.

Figure 1:
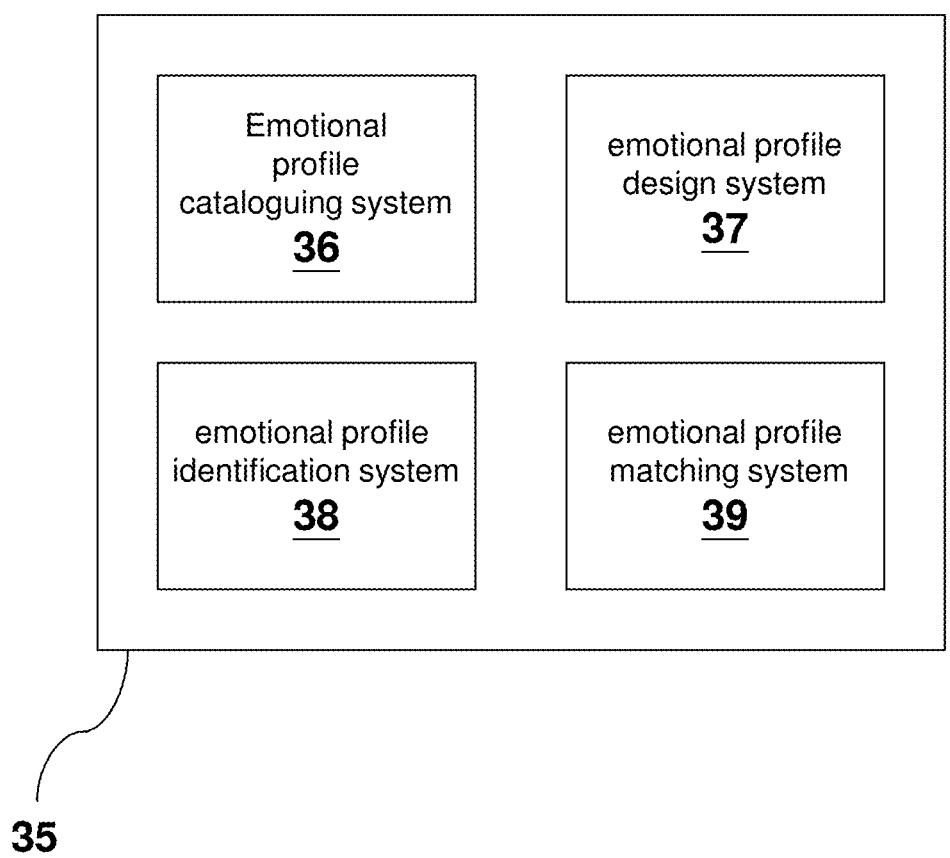
FIG. 1 depicts the main application software systems of the computerized emotional profiling server according to one example of the present invention.
Figure 2:
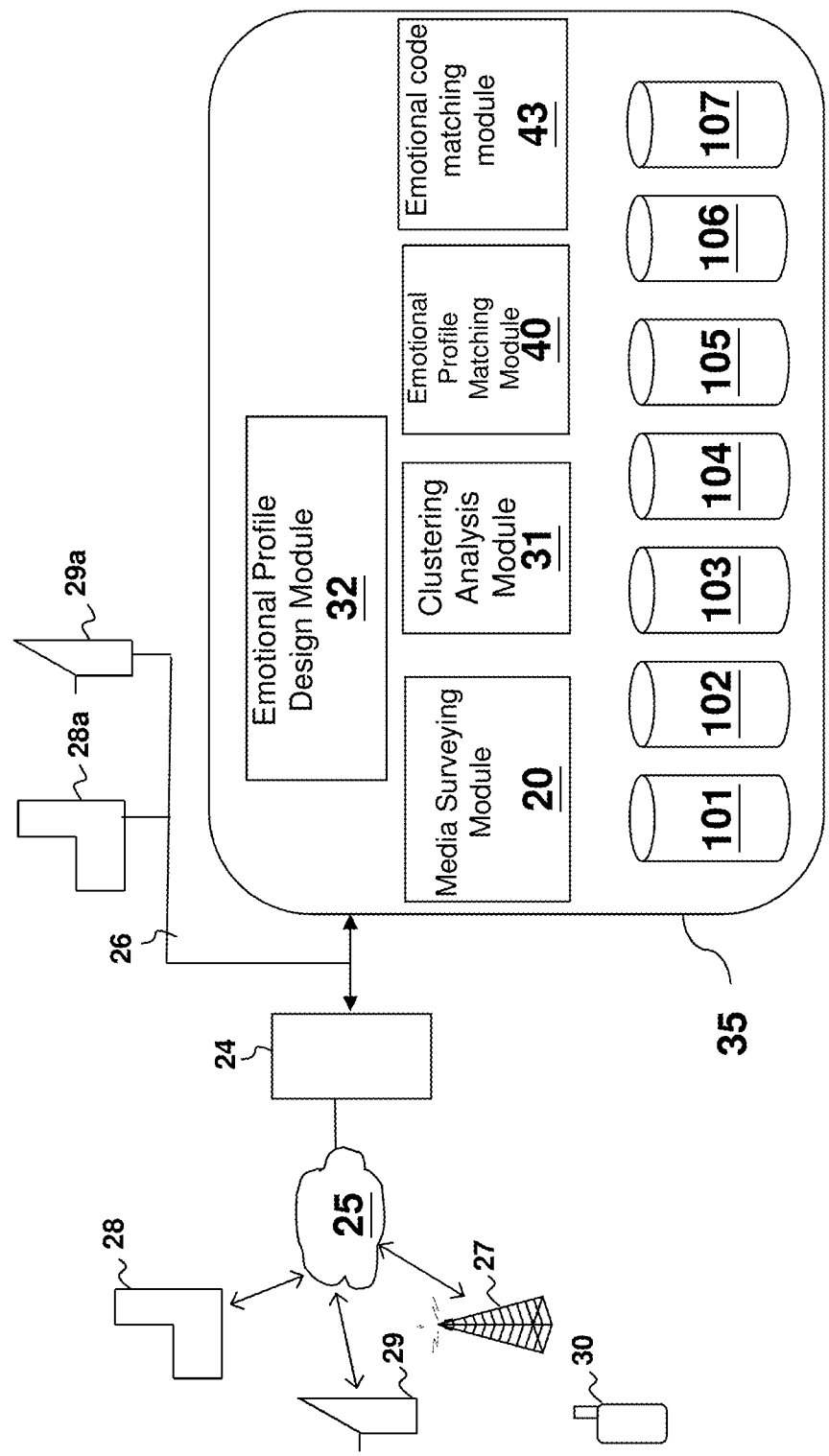
FIG. 2 shows the major software modules and databases of the computerized emotional profiling server according to another example of the present invention.

Referring now to FIG. 1, the first embodiment of the present invention is a computerized emotional profiling server (35) that offers a suite of functions for conducting an emotional profile survey. This computerized emotional profiling server (35) further comprises hardware modules and application software systems to provide the services. The hardware modules will be described later. The software systems comprise (a) an emotional profile cataloguing system (36) that sends out emotional survey forms to users, collects the survey results and clusters the results into emotional categories; (b) an emotional profile design system (37) that helps a designer to design a multi-media message that appeals to the emotional preference of a targeted user community; (c) an emotional profile identification system (38) that categorizes a new entity to the emotional categories found by the emotional profile cataloguing system (36), and (d) an emotional profile matching system (39) that matches the emotional profile of a new entity against existing entities. In one implementation, all these four systems are implemented using a common set of software modules and utilizes a common set of databases to store the relevant information. These common modules and databases are shown in FIG. 2. The media survey module (20) is to send out an emotional survey form to a plurality of users. It does so by first identifying a survey document from the survey document database (105). The survey document contains a plurality of survey forms. Each of the survey form consists of at least one survey question and a plurality of multi-media objects; both of which are drawn from the multi-media presentation database (103). A name-list database (104) is used to supply user names to the media survey module (20). The name-list database (104) may contain a plurality of user communities; each user community comprises a plurality of user names for the media survey module (20) to send the survey form to. In a specific embodiment, the user communities may be a Yahoo group, a MSN community, eBay, Loyalty Marketing Group, Direct Mailing Group, and the likes.

The media survey module (20) also collects the choices that the user has made in answering the survey questions. Other relevant information such as the speed of answering, the multiple choices that the user selected, is also captured to create the survey result record for this user. The survey result record is then stored onto the survey result database (101) for the cluster analysis module (31) and other modules to access. The cluster analysis module (31) segregates the survey result records into multiple clusters or emotional profile categories. (The term 'cluster' and 'emotional profile categories' are used interchangeably here.) Each cluster represents a segment of users that have similar emotional profile and is assigned an emotional code. All users in that segment are then tagged with that emotional code. The emotional code, as well as other clustering information, is stored as one emotional profile record in the emotional profile database (102). The emotional profile design module (32) is to facilitate a designer to design and progressively refine a multi-media message for a targeted user community. After analyzing the result of a general survey, special survey forms with specific questions can be designed to extract the distinct emotional profile of this targeted user community, and the result is used to compose a new multi-media message.

The emotional profile matching module (40) is to tag a new user with an existing emotional code and the emotional code matching module (43) is to match an emotional code input to the system against existing entries in either the personal emotional code database (106) or object emotional code database (107).

FIG. 2 also illustrates one embodiment of the invention on the way the computerized emotional profiling server (35) interacts with the user and/or the designer. In a typical implementation, the computerized emotional profiling server (35) is connected to a data communication network. In a preferred embodiment, it is a local area network (26). The local area network (26) connects to a web server (24) and also connects to other computing equipments such as the desk-top computer (28a) and the information kiosk (29a) shown in FIG. 2. Similarly, other desk-top computers (28), information kiosk (29) and portable wireless devices (30) can also access the computerized emotional profiling server (35) via the Internet (25) through the web server (24). The portable wireless device (30) can be a mobile phone, a smart-phone, or a PDA-phone that can be connected to the Internet (25) via the mobile operator (27).

It is clear to those skilled in the art that there are many ways to interconnect the computerized emotional profiling server (35) to many different kinds of computing devices that the user or designer use. The teaching shown in FIG. 2 should not be construed as the only way to implement this invention. For example, the computing device can be but not limited to an information kiosk, desk-top computer, lap-top computer, palm-top, PDA, data-tablet, smart-phone, interactive TV, Internet TV or any other devices that can prompt the user or designer a message and solicit a response from them. The data communication network can be but not limited to the Internet (25), a cellular wireless network, a wired local area network (LAN), a wireless LAN, wired or wireless metropolitan area networks, or any combination of the above.

Furthermore, the computerized emotional profiling server (35) may be implemented in a distributed computing environment whereby some of the software modules are installed and run on separate computing platforms. As a specific example, the media survey module (20) can be installed on the desktop computer (28) or the information kiosk (29) across the Internet (25). In this case, the survey is conducted in a remote location and the survey result record is transferred back to the computerized emotional profiling server (35) and is stored in the survey result database (101) herein. Likewise, other software modules can be installed and run on separate computing platforms.

In one embodiment of the present invention, common modules (20), (31), (32), 190 and (40), and (43) in FIG. 2 are selectively chosen to implement the four application software systems (36), (37), (38) and (39) as shown in FIG. 1. The following sections teach the inventive ideas of each software systems; and how this can be realized by the common modules.

Figure 3:
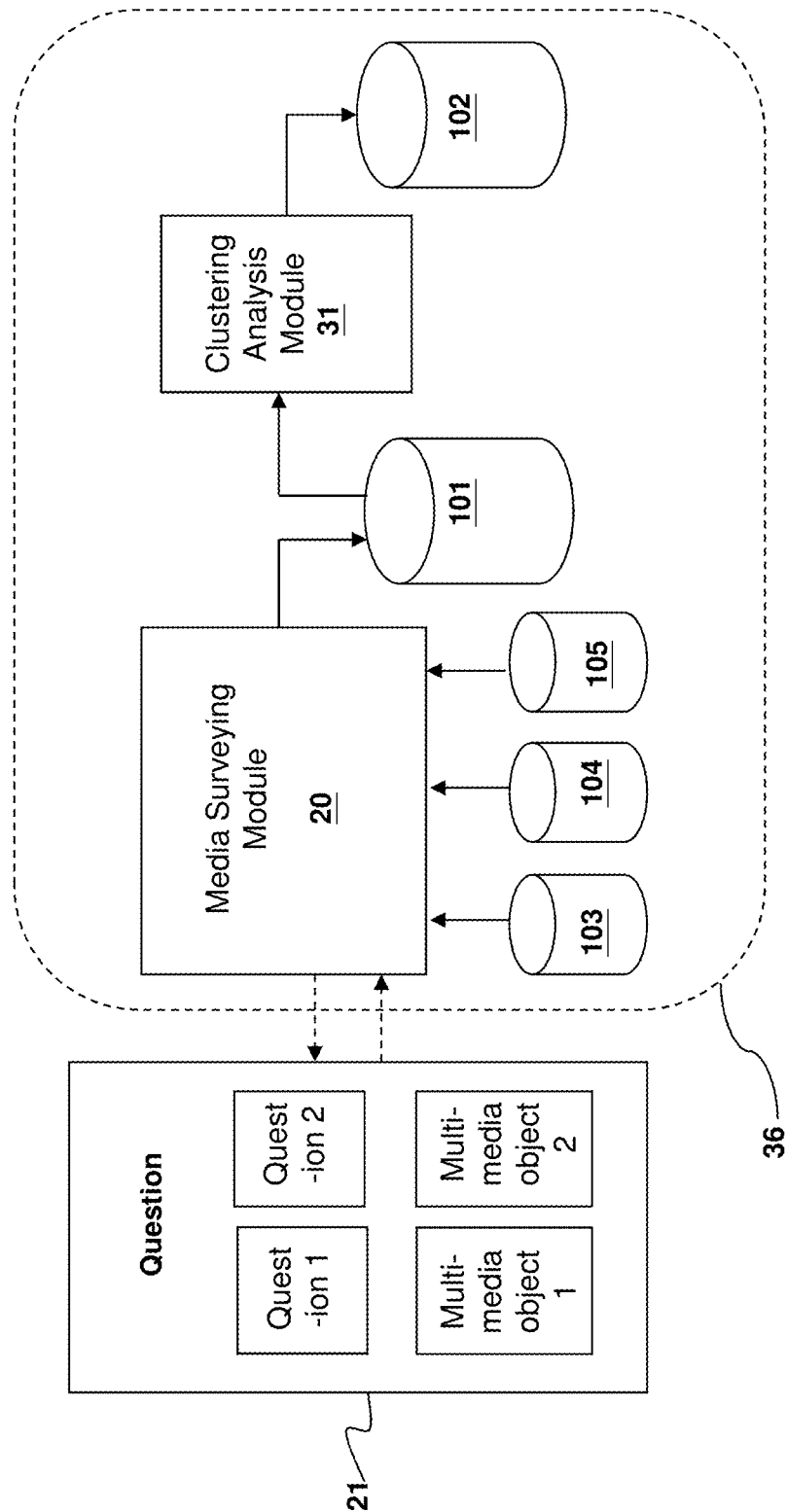
FIG. 3 is the architecture diagram of the emotional profile cataloguing system according to yet another example of the present invention.
Figure 4:
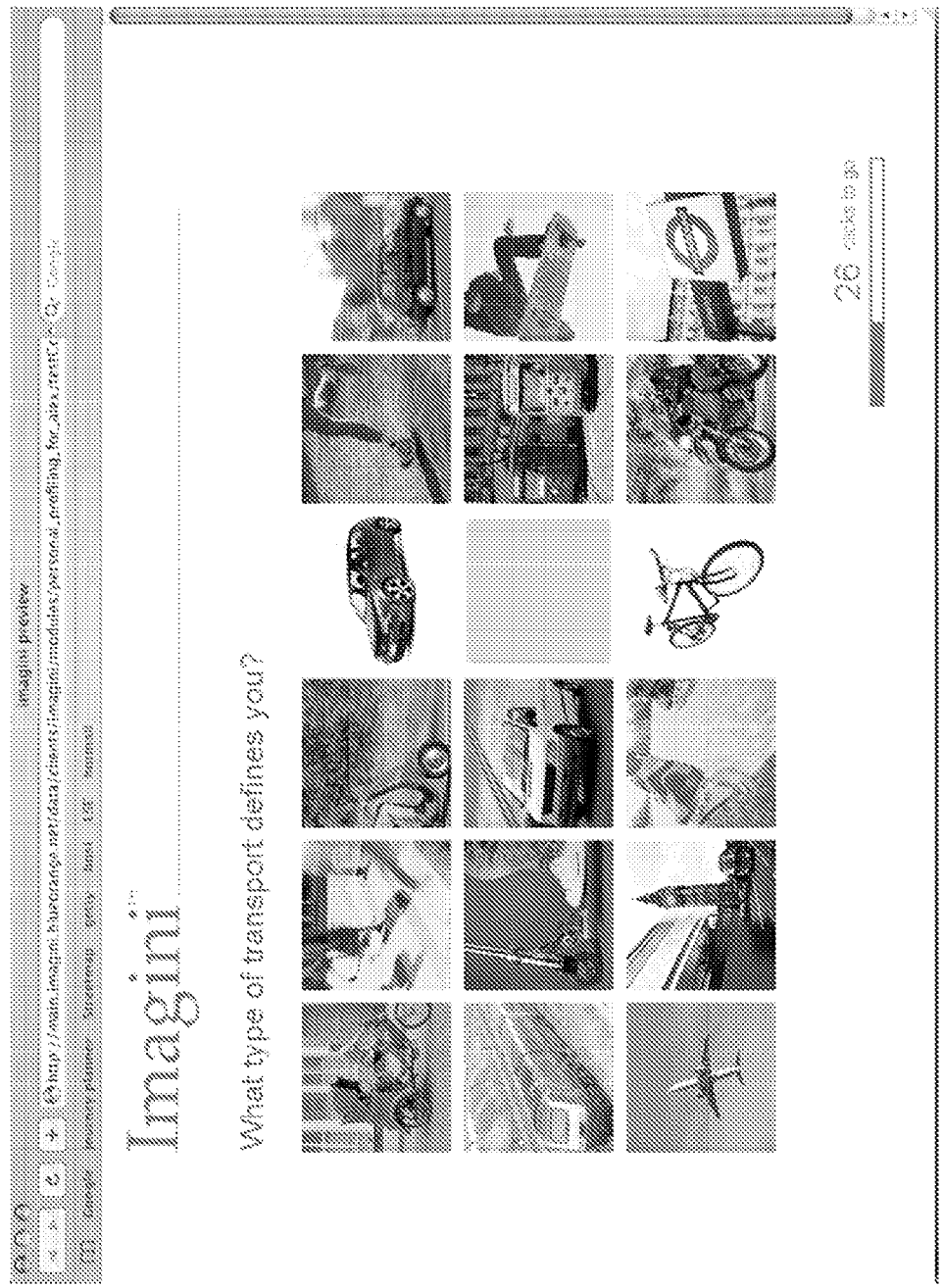
FIG. 4 is an example of the emotional survey form according to another example of the present invention.

FIG. 3 illustrates one implementation of the emotional profile cataloguing system (36), which is one of the services that the computerized emotional profiling server (35) provides. This system makes use of the media survey module (20), the cluster analysis module (31), and the five databases (101), (102), (103), (104) and (105) to realize the profile cataloguing operation. The media survey module (20) sends out a survey form (21) to a user and prompts the user to choose one or more answers. The survey form (21) comprises at least one question together with a plurality of multi-media objects. Typically, the question is a textual message. The multi-media object can be but not limited to a textual object, an image, photograph, picture, audio clip, sound clip, movie, or any combination thereof. When the multi-media objects are textual objects, then the survey form is similar to a traditional text-base survey form. In a preferred embodiment, the survey form is displayed on the web browser of the user's computing device. A typical web browser is the Internet Explorer from Microsoft. FIG. 4 shows a typical survey form whereby the multi-media objects are image objects. In yet another preferred embodiment, the image is a mouse-clickable object so that when the user clicks on a particular image, the web-browser detects which image the user has chosen and sends this information back to the media survey module (20) as the user's choice of that survey question.

The survey document database (105) comprises a plurality of survey documents. Each document is intended for a specific application domain and comprises a set of survey forms. For example, one survey document may be for the leisure domain while another one is for the interior home decoration domain. The survey form may be entirely text-based (i.e. the multi-media objects are text objects). This kind of survey form is to record the factual and demographic information about the users such as their sex, age range, income level and the likes. This is the traditional survey questionnaires. An important aspect of the present invention is not only to gather demographic information from the user but also his emotional preferences. Hence in a typical survey document, the survey forms comprise not only pure text-based forms but also forms with rich multi-media objects such as the one shown in FIG. 4. Research has shown that when pure text-based questionnaires are presented to a user, the user will go through a 'considered thought process' to read up the multiple choice answers before he selects the one that is applicable to him. However, it is well known that feelings drive a vast majority of human behavior and choices, and how people feel in the test environment is closer to how they would feel and act in real-life. This kind of inner feelings can better be captured by user's direct emotional response to visual stimuli. Hence a survey form comprising a plurality of images or visual objects (hereafter also referred to as a mood board) can capture the emotional reflex of the user that can not be done by conventional text-based questionnaires.

Figure 5:
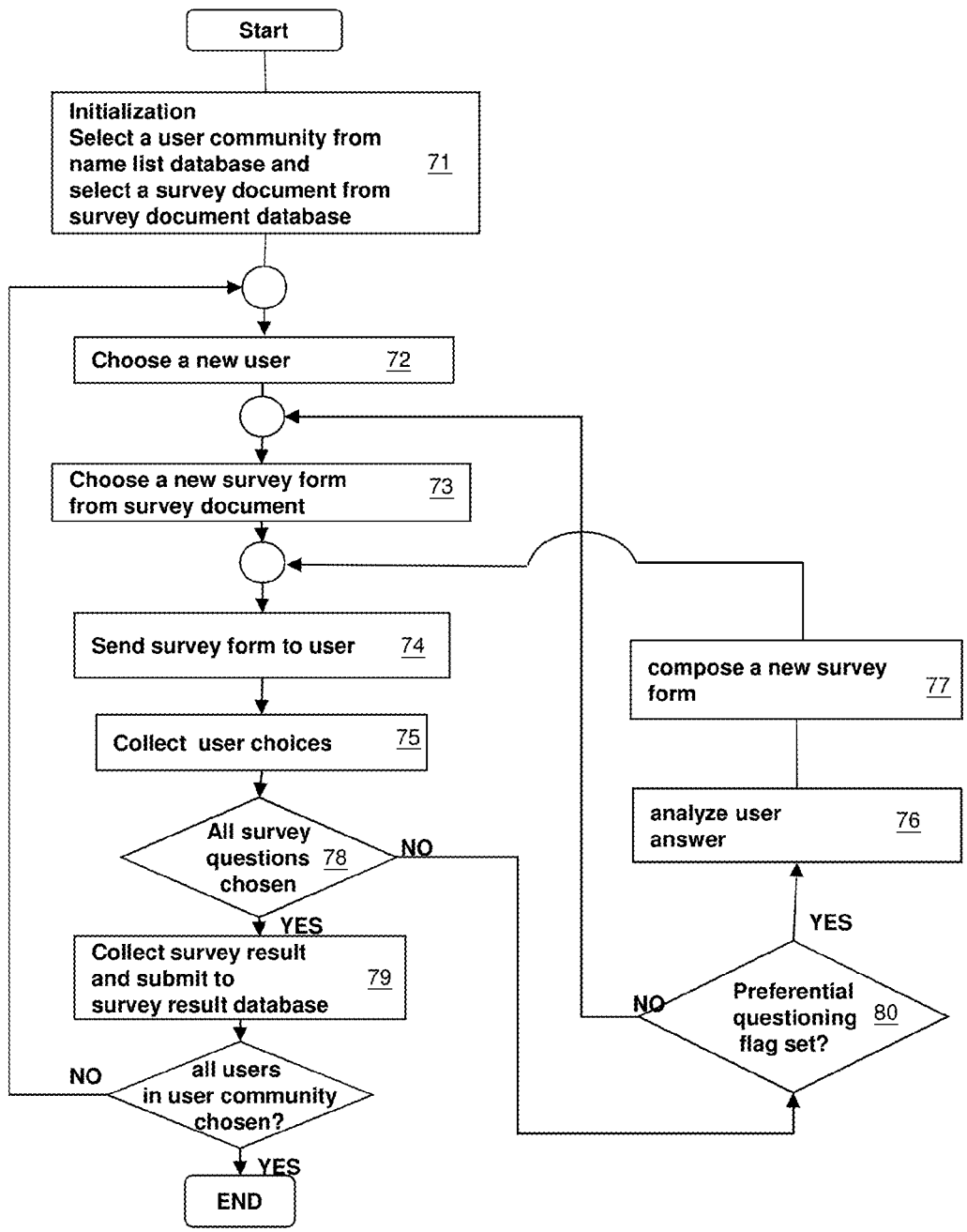
FIG. 5 is a program flow diagram for the media survey module according to another example of the present invention.

In a preferred embodiment, the operational flow-chart of the media survey module (20) is depicted in more details in FIG. 5. When this module is invoked, it will first go through the initialization process (71). This includes selecting a user community from the name-list database (104), and a survey document from a survey document database (105). Afterwards, it will choose a new user from the user community in step (72), and then choose a new survey form from the survey document in step (73). Next, it sends the survey form to the user in step (74) and collect user's choices in step (75). The user may select one or more choices. These choices, together with the speed of making the choices are captured by this module. If multiple choices are selected, the sequential order of these choices is also recorded. Since the inventive system is to capture the emotional reflex of the user, the speed, and the ordering of the choices reveal much information about the user's emotional preferences and hence is important information for subsequent analysis.

Afterwards, it will check if all the survey forms have been sent to this user in step (78). If not, it further tests whether the 'preferential questioning flag' is set in step (80). If not, then it will go back to step (73) to choose a new survey form to send to the user, and the program loop is repeated.

The 'preferential questioning' is a special feature of this invention. If this flag is set, control is passed to step (76) and the user's choice to the current survey form is analyzed. Depending on the user's choice, a new survey form may be composed that is tailored to the user's specific answer. The new survey form is composed in step (77) and then control is passed to step (74) as shown in FIG. 5. Hence with preferential questioning, survey forms may be generated dynamically depending on user's previous choice and the survey result will better reflect the user's specific emotional reflex.

In step (78), if all the survey forms have been presented to the user, control is passed to step (79). The survey result, which comprises all the choices made by this user, together with the speed of making these choices and all other relevant information, is stored onto the survey result database (101) as a survey result record. This module will then check if all users in the chosen user community have been processed. If not, control is passed to step (72) and a new user is chosen. Otherwise, the program exits this module.

After all the survey result records from the user community have been collected, the emotional profile cataloguing system (36) invokes the cluster analysis module (31) to analyze them. In general, the survey result record has a complex data structure in order to store the multi-facet demographic data and emotional preferences of the user. It may be implemented as a high dimensional matrix, a tree structure or an object-oriented data type. In one implementation, it comprises a vector that records the demographic data of the user, and a multi-dimensional matrix that records his emotional preferences. The multi-dimensional matrix may further comprise the choice vector that registers the choices made by the user, the speed vector to record the time it takes for the user to make that choice(s) and the sequential ordering vector that registers the ordering of choices if the user selects more than one choice for a question. In a simplified implementation, it is a multi-dimensional vector and statistical clustering technique is used to perform clustering analysis on these multi-dimensional vectors. As a typical example, this module can invoke the SPSS statistical package from SPSS Inc. The cluster analysis module (31) produces at least one cluster from the survey results; and also the statistics associated with this cluster.

Figure 6:
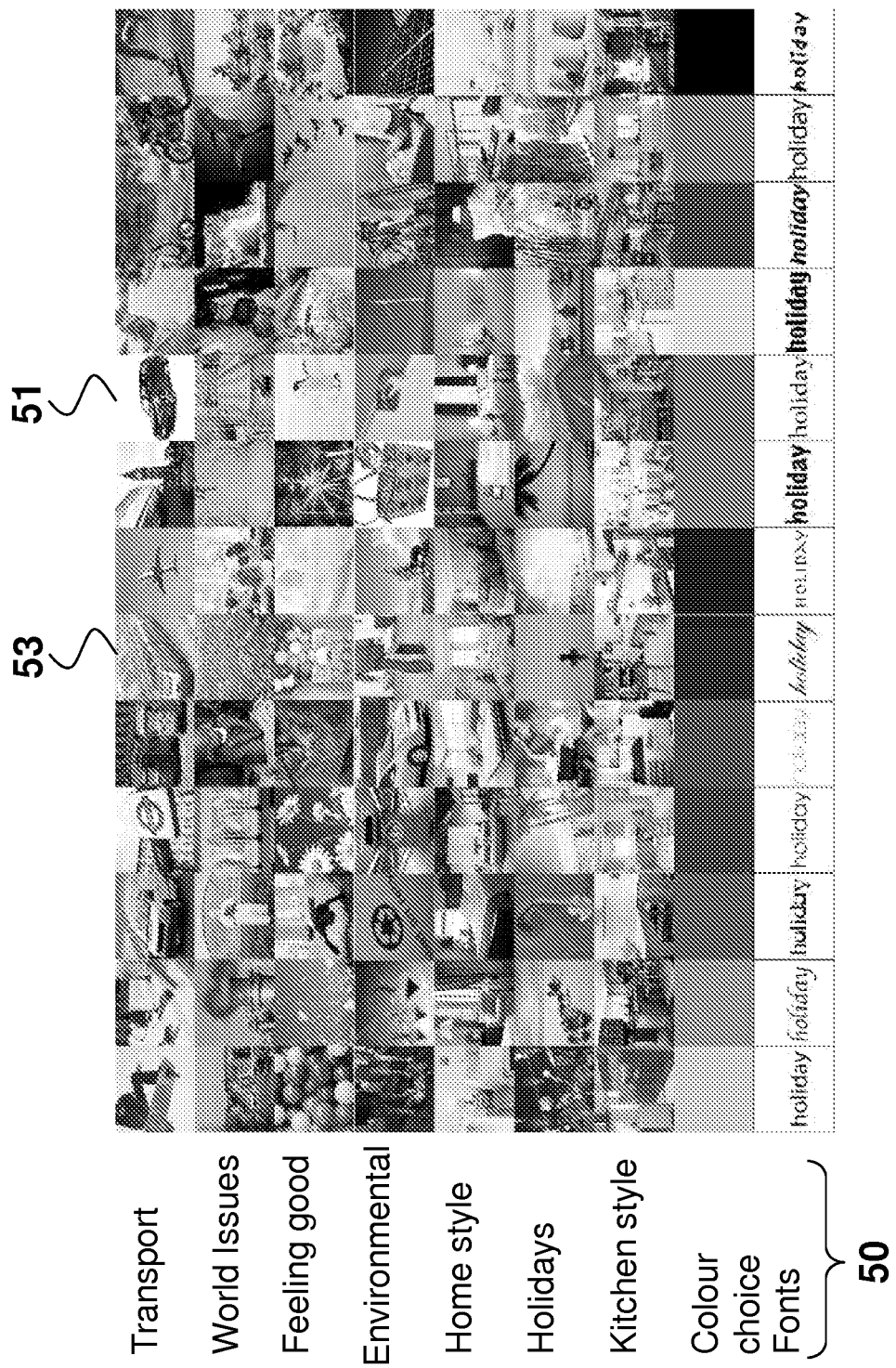
FIG. 6 is a simplified view of a survey document.

To further illustrate how the clustering module performs the emotional profile cataloguing, a specific example is given here. FIG. 6 is a simplified view of the survey document. The first column (50) with single-word labels 'transportation', 'world issues' . . . etc is an abbreviated description of the survey questions. For example, the first question, about transportation may be "Which mode of transportation do you like best?". The first row is the images about the modes of transportation for user to select. Here image (51) is the image of a car and image (53) is the image of a train. The first survey form therefore comprises a question about 'transportation' and also the thirteen images from the first row of images in FIG. 6. Likewise, the second survey form comprises a question on world issue such as "Which picture captures best the most important world issue today?" and the thirteen images from the second row of images in FIG. 6.

There are nine survey forms in this survey document illustrated in FIG. 6. The survey result record in this case is a multi-dimensional matrix of 3 rows and 117 columns. As there are 9 survey forms and 13 images in each form in this survey document, there are 117 (9×13) selectable choices. Each column corresponds to one choice. The first row of the multi-dimensional matrix stores the choice(s) that the user makes. Notice that the user can select more than one choice in one question. The second row records the time it takes for the user to make the choice(s) and the third row stores the sequential ordering of choices if more than one choice is chosen by the user.

Figure 7:
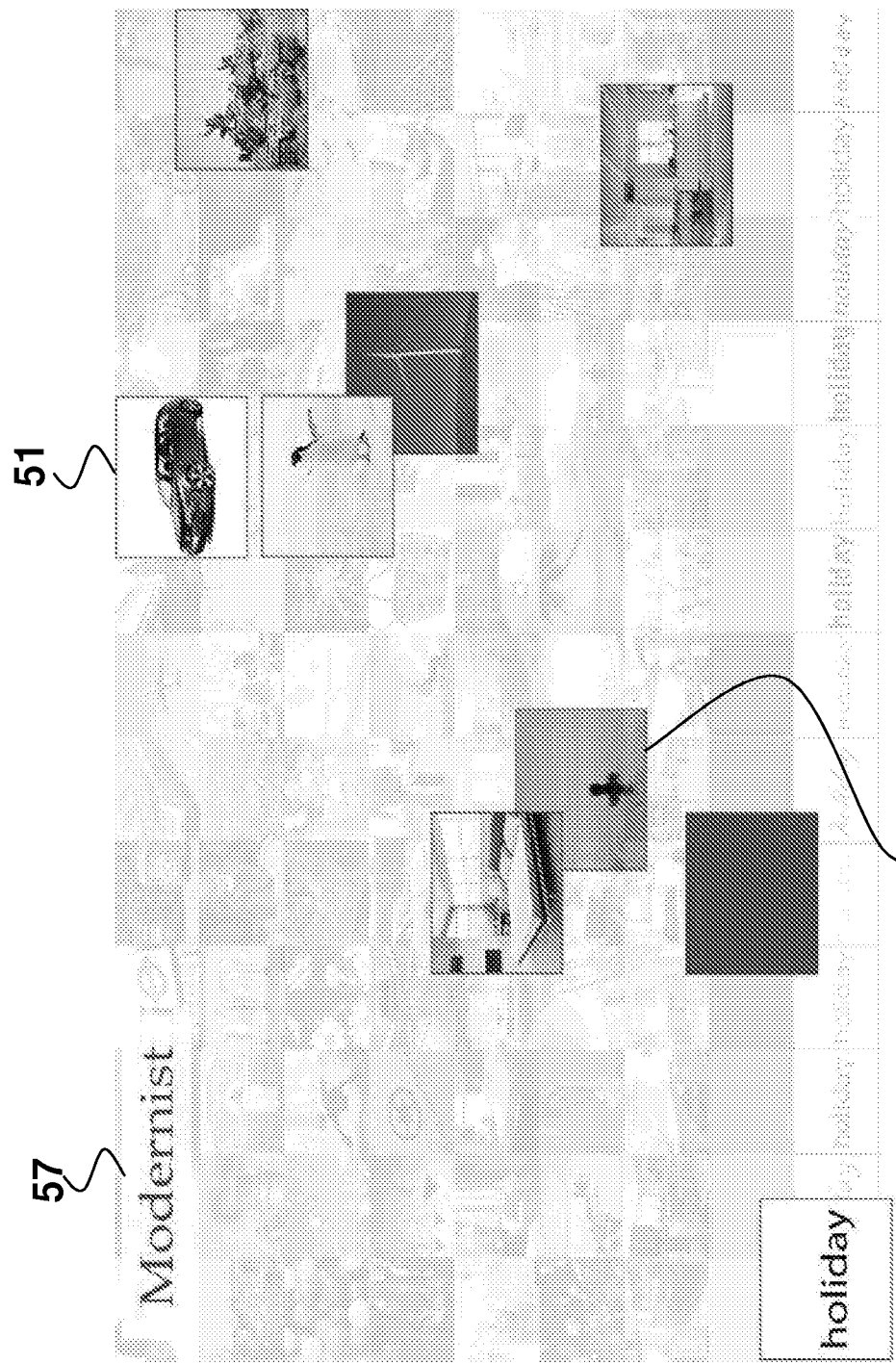
FIG. 7 shows the first emotional profile category.
Figure 8:
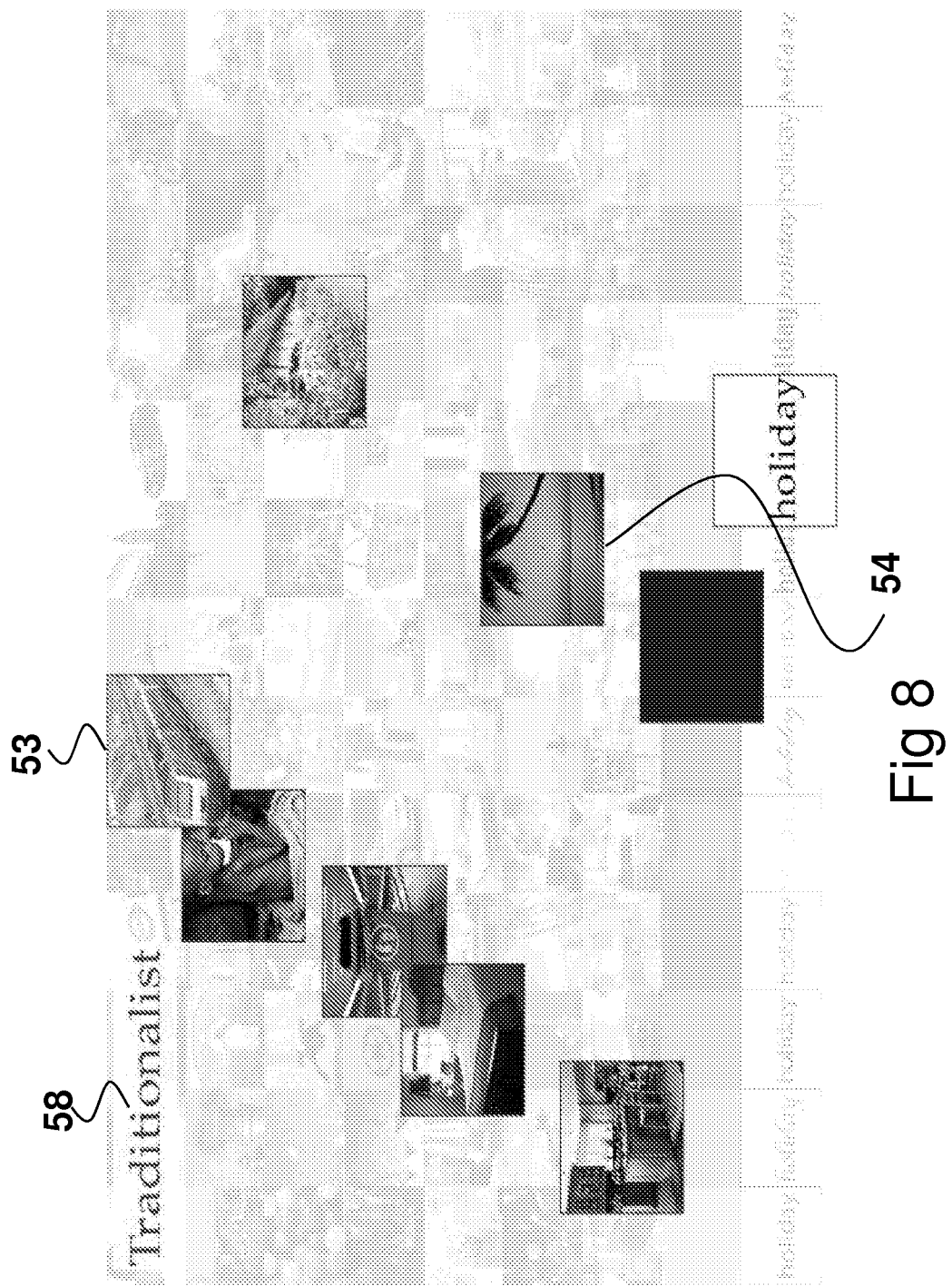
FIG. 8 shows the second emotional profile category.
Figure 9:
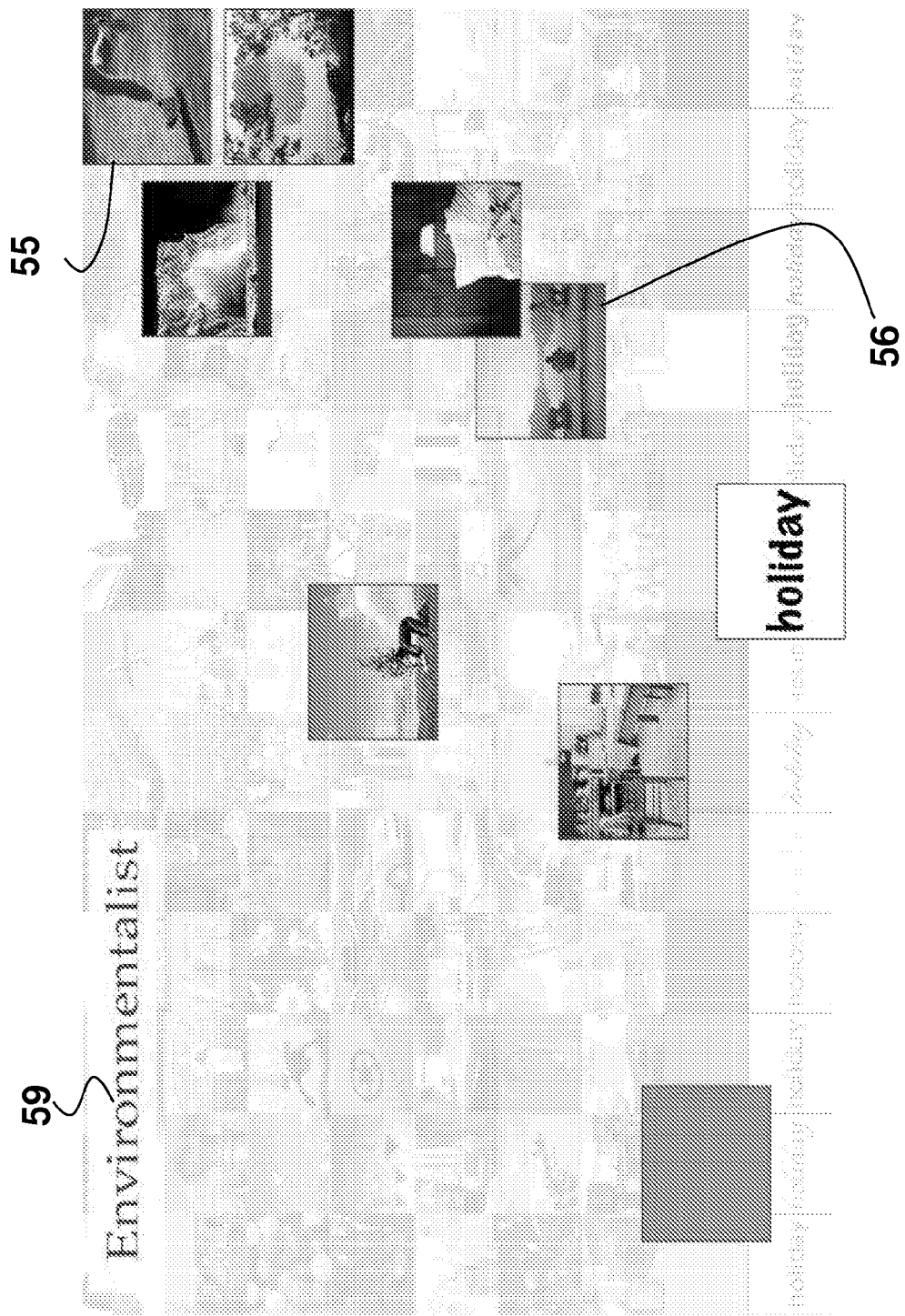
FIG. 9 shows the third emotional profile category.

In operation, the cluster analysis module (31) shown in FIG. 2 retrieves all the survey result records from the survey result database (101) and segregates them into clusters or emotional profile categories. As an illustrative example, three emotional profile categories are produced after the clustering analysis, together with a set of cluster statistics associated with each category. FIG. 7 illustrates the first emotional profile category. The majority of users in this category choose the image of the car (51) for 'transportation' and image (52) for the question on 'holiday'. Notice that there is one image chosen in each row; and these images are the most popular choices among the group of users in this category. Likewise, users in the second emotional profile category choose the image of a train (53) for transportation and sunset (54) for holiday as shown in FIG. 8; and users in the third emotional profile category choose images (55) and (56) for the questions on transportation and holiday respectively in FIG. 9. By observing the choices of each group of users, a designer can then assign an emotional code to each category. For example, users of the first category can be labeled as modernist (57), those of the second as traditionalist (58) and the third environmentalist (59). Alternatively, an arbitrary code may be used for each category, e.g. users of the first category can be labeled as category A, those of the second as category B and users in the third labeled as category C. This clustering statistics, together with the emotional code, and all other relevant information related to this emotional profile category are stored as an emotional profile record in the emotional profile database (102).

After clustering, users in the same emotional profile category can then be assigned to the same emotional code. This code becomes the personal emotional code of this segment of users. As it denotes the emotional preference of the user, it is also referred as his emotional fingerprint. It is advantageous to use an easy-to-remember name or image to denote the emotional code for future references. In the first example given, the names 'traditionalist', 'modernist' and 'environmentalist' are used. This can become the international emotional code; and when this emotional code is adopted worldwide, it can greatly improve the efficiency of the consumer/commerce communication as will be seen by way of examples in subsequent paragraphs. Alternatively, a very long numeric code containing the information of the specific preferences relating to the matrix described above. Many other ways of coding may be devised by a user based In another aspect of the present invention, the emotional code of an object such as a company, a service, a product, or a brand, a movie or music is determined Though these objects are not human subjects that exhibit emotion, it is nonetheless possible to study the users who use, view, purchase, possess, or own the object and arrive at the emotional code of this object. As a typical example, the following method can be used to determine the emotional code of a department store. Firstly, data can be collected for those who patronize this department store. In this example the patrons of the store become the predetermined criteria by which the user community is assembled. The personal emotional codes of these patrons can then be tallied up; and the code that has the highest number of patrons can be used as the emotional code of the department store. This is but just one method of determining the emotional code of an object and is referred as the object emotional code. Accordingly, those skilled in the art may devise many other variant schemes to determine the object emotional code and that will generally fall into the scope of this invention. When a user is tagged with his personal emotional code and an object tagged with its object emotional code, many new applications can be developed to make use of this inventive concepts. Both the personal emotional code and the object emotional code can be stored to their respective personal emotional code database (106) and the object emotional code database (107) as shown in FIG. 2.

Figure 10:
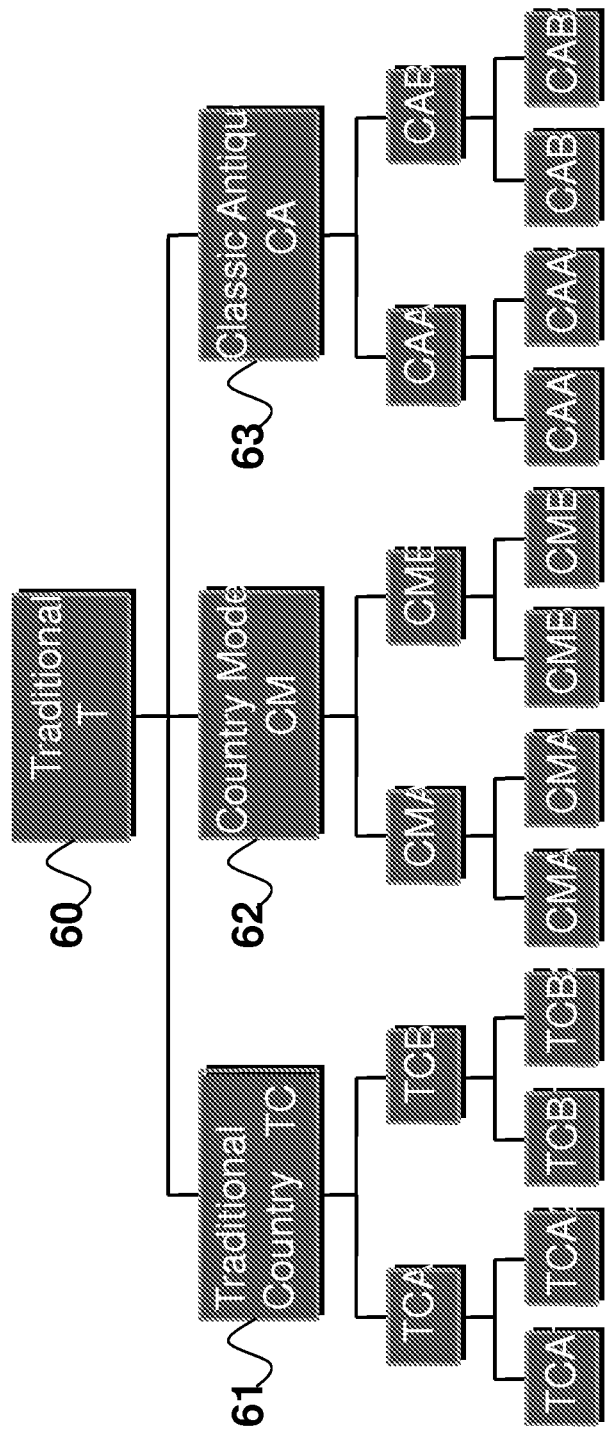
FIG. 10 illustrates the segmentation tree structure of emotional profiles and emotional codes.

In yet another preferred embodiment, the cluster analysis module (31) can be used to obtain sub-emotional categories of a user segment. Recall that the cluster analysis module (31) is used to segregate the plurality of users into at least one user segment, and each segment is assigned to an emotional code. By feeding a user segment to the cluster analysis module (31) again, a more refined emotional sub-categories can be obtained. In essence, the user segment is segregated into smaller sub-segments, each of which can be assigned a more specific emotional code. This is shown in FIG. 10. The original user segment with emotional code 'traditional (T)' (60) can be further segmented to three sub-categories, each of which are tagged with a more specific emotional code—namely, 'Traditional Country (TC)' (61), 'Country Modern (CM)' (62) and 'Classic Antique (CA)' (63). Likewise, each of these sub-segments can be further segregated into sub-sub-segments as shown in FIG. 10. And the corresponding emotional code becomes more and more specific in describing the emotional profiles of that user segment. Clearly, alternative codes, such as but not limited to a string of numerals or bytes may be used to represent them.

Figure 11:
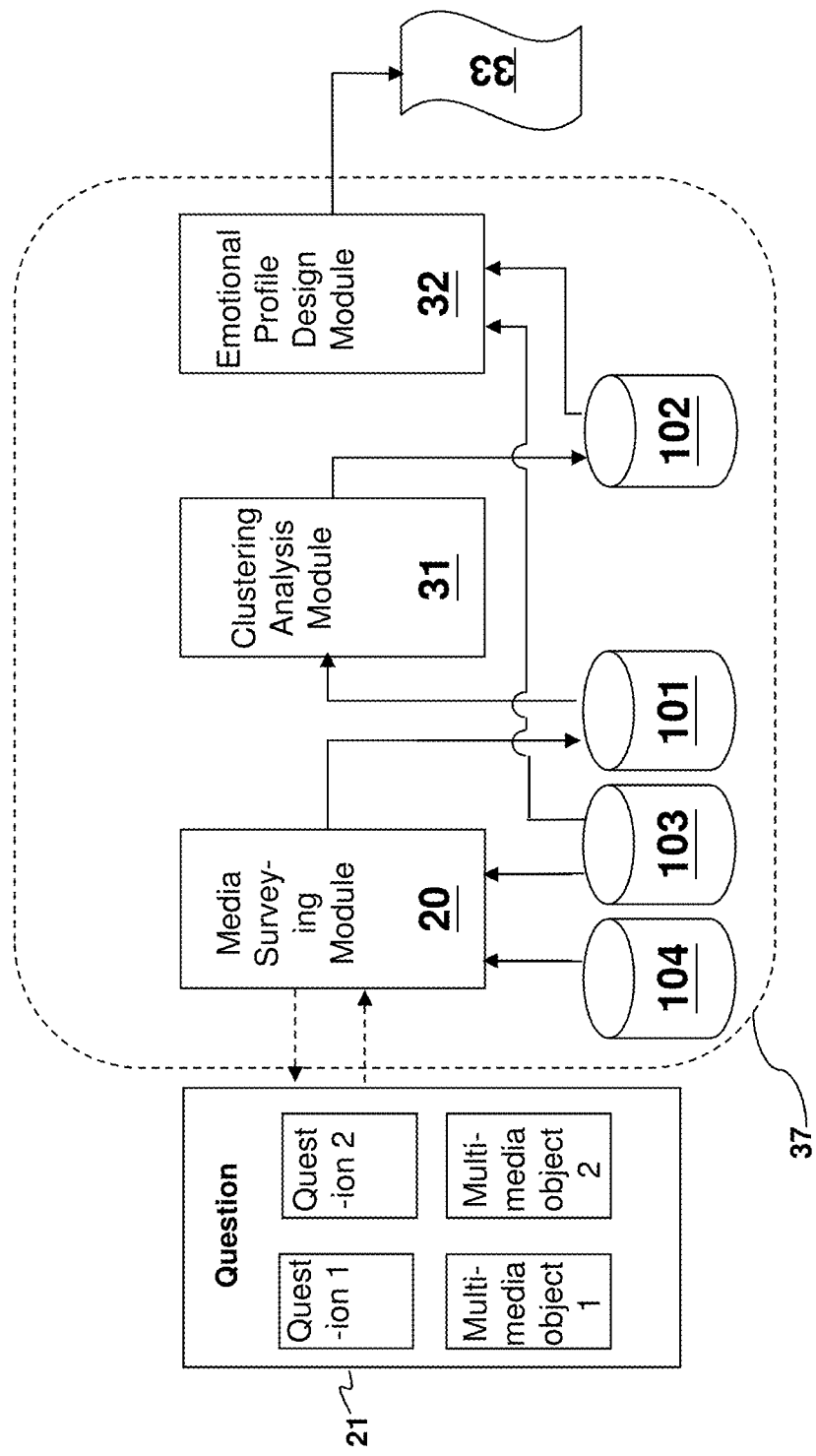
FIG. 11 is the architecture diagram of the emotional profile design system

The emotional profile design system (37) comprises the emotional profile design module (32) and those modules and databases that are used in the emotional profile cataloguing system (36) as shown in FIG. 11. The objective of this system is to assist a designer to arrive at a multi-media message (33) that appeals to the emotional preference of a targeted user community. In a specific embodiment, the multi-media message (33) comprises a message that a company wants to convey to the user community and a multi-media object drawn from the multi-media database (103). In a preferred embodiment, the multi-media object is an image, a picture or a photograph. This image will arouse the instinctive emotional reflex of the targeted user so that he is attracted to pay more attention to the message. In operation, the designer first makes use of the clustering result from the emotional profile cataloguing system (36) to understand the emotional preferences of a general user community. He then uses the emotional profile design module (32) to select an emotional profile category from the emotional profile database (102) that he wants to target, and find the multi-media object that is most popular to this user group to compose the multi-media message (33). After presenting this multi-media message (33) to the users in this emotional profile category for a while, a new survey can be conducted on this group with a new survey document that asks more specific emotional preferences questions. After a new set of survey result records are obtained from this user group, the cluster analysis module (31) can be invoked again so that sub-categories of emotional profile can be obtained. The sub-categories of emotional profile are a refinement of the previous ones and can describe the emotional preferences of this user group with better precision. With a more precise emotional profile, the designer can then re-design the multi-media message that appeals to this group. This process can be reiterated so that the designer can better understand the emotional preferences of his targeted user community.

Figure 12:
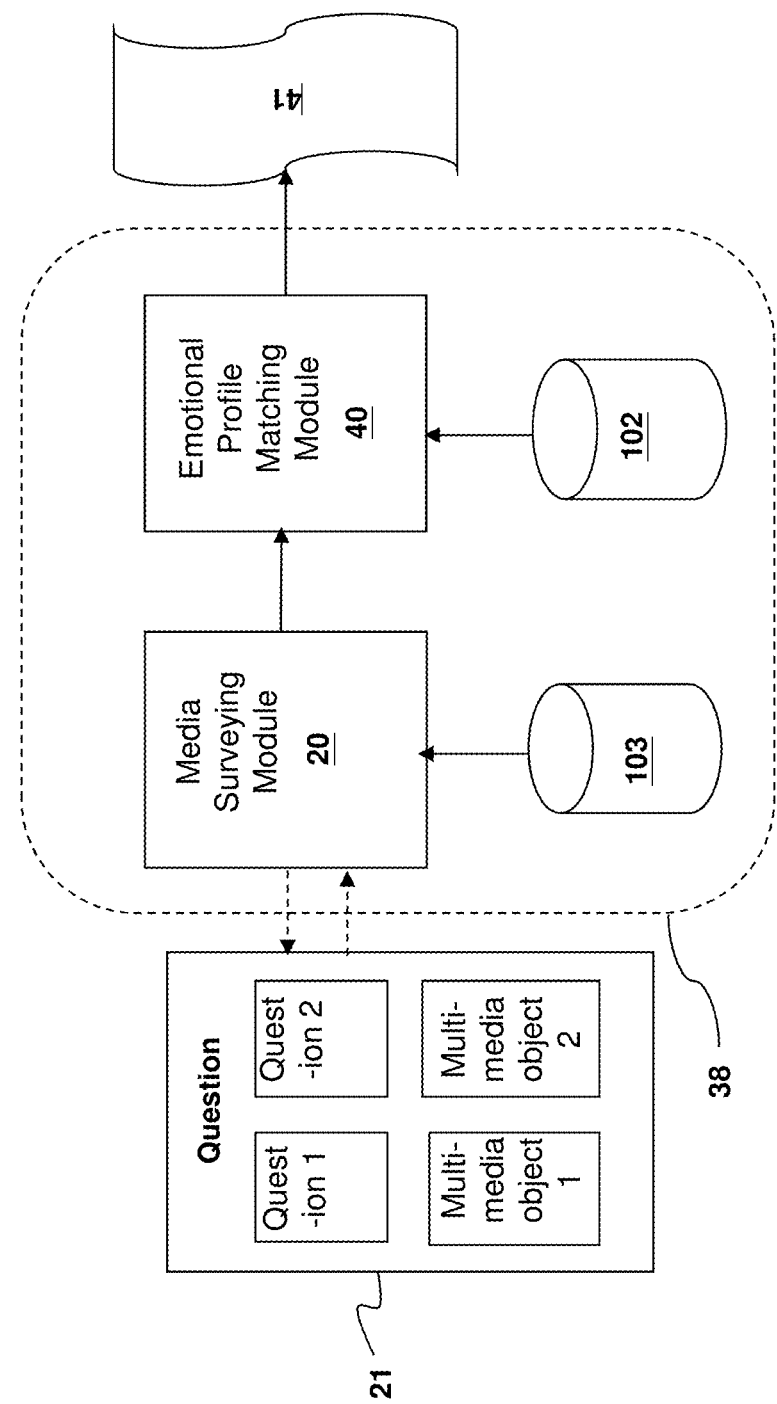
FIG. 12 is the architecture diagram of the emotional profile identification system.

The emotional profile identification system (38) comprises the media survey module (20) and the emotional profile matching module (40), and accesses the multi-media database (103) and the emotional profile database (102) as shown in FIG. 12. In one implementation, this system first sends survey forms (21) to a new user and collects the survey result record from him. Then it computes matching scores between the survey result record and all the emotional profile records in the emotional profile database (102). If the matching score satisfies a pre-defined criterion, the system will assign the new user to the corresponding emotional profile category and his personal emotional code will be tagged accordingly. The operation flow of the media survey module (20) to collect the survey result is the same as previously discussed and is not repeated here. The emotional profile records, in one specific implementation, comprises an emotional code, the user segment associated with this emotional profile category, and also the cluster statistics computed from the cluster analysis module (40). These emotional profile records are obtained from previously-conducted surveys on the user community. Using the previous example as an illustration, part of the survey result record is the choice vector (63) of 117 elements, each of which is set to '1' if chosen by the user; otherwise, it is set to zero. The emotional profile category also has a corresponding vector of similar dimension. The value of each element in this vector is the total number of times this choice is selected by the ensemble user community. The matching score can simply be the inner product (or dot-product) of the two vectors, normalized by the number of choices the new user selected in his survey result record. Alternatively, other methods to compute the matching score can be developed. As an illustration, one can partition the 117 element vector into 9 regions, each of which corresponds to one survey question. Within each region, it further selects the highest value and assigns the corresponding vector-element to one, with the rest reset to zero. This is equivalent to selecting the most popular choice within one question as representative of that question. Afterwards, the inner product is computed and the result is the matching score.

It is clear to one skilled in the art that many alternative ways to compute the matching score can be devised and they will not be elaborated here. It suffixes to illustrate that a matching score can be computed between the new user's survey result record and the emotional profile record, and this score is then stored as one entry in the matching list (41).

Figure 13:
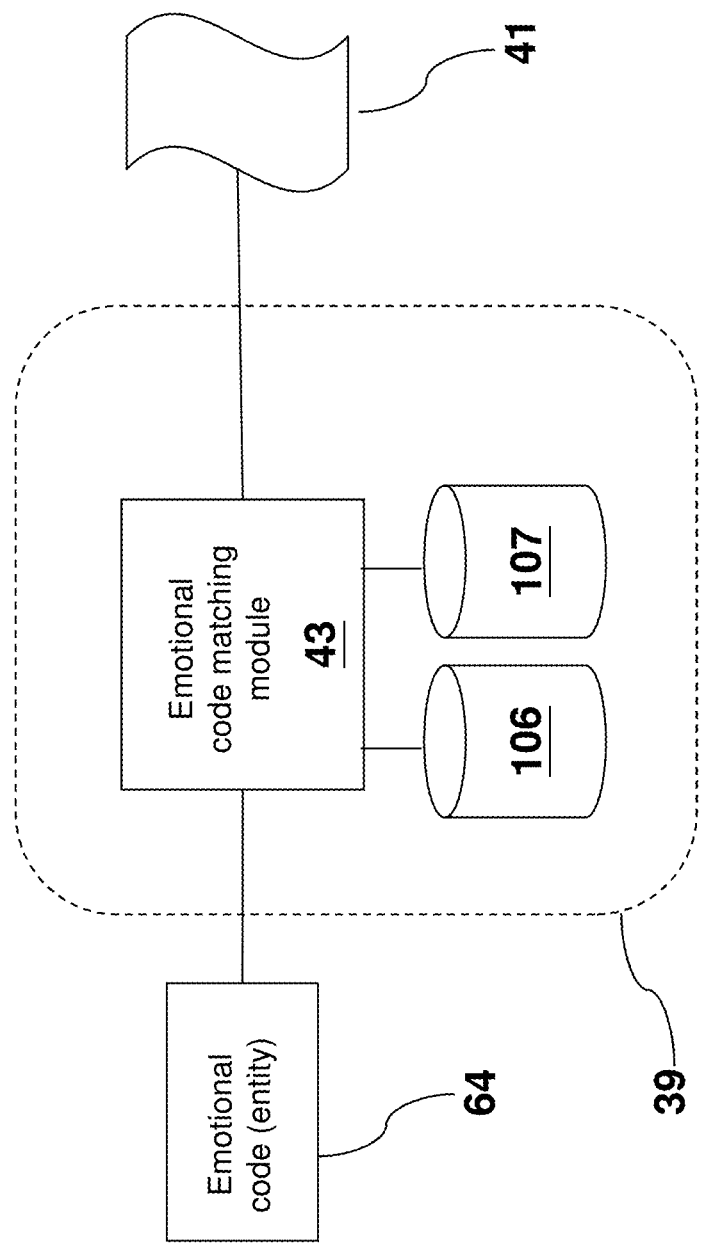
FIG. 13 is the architecture diagram of the emotional profile matching system.

After all the emotional profile records in the emotional profile database (102) are processed, the matching list (41) is sorted in descending order. In one preferred embodiment, the pre-defined criterion mentioned above is an absolute threshold. In this case, the user is assigned to the corresponding emotional codes whose matching scores are higher than the absolute threshold. In another preferred embodiment, the pre-defined criterion is the top-N entries of the matching list (41), where N is a numerical integer between one and the size of the matching list, and is specified by the designer. As an example, assuming that the highest matching score corresponds to the emotional profile record whose emotional code is 'traditionalist'; and the second highest score corresponds to the emotional code 'environmentalist'. Then if N is 2, the new user is assigned to both a 'traditionalist' (top score) and an 'environmentalist' ($2^{nd}$ top score). But if N is 1, he is assigned to the 'traditionalist' only. Hence after going through the survey, each new user is assigned to at least one emotional code. This emotional code becomes his personal emotional code—or Emotional DNA The emotional profile matching system (39) is to match the emotional profile of a new entity with an existing entity. It comprises the emotional code matching module (43) and both the personal emotional code database (106) and the object emotional code database (107) as shown in FIG. 13. As mentioned previously, an entity can be a person or an object such as a company, a product, a service, or a brand. This module is capable of (a) matching between two personal emotional codes, (b) matching a personal emotional code against an object emotional code, or (c) matching between two object emotional codes. In operation, the emotional code (64) of a new entity is input to this system. It is used to match with records in either the personal emotional code database (106) or the object emotional database (107) to produce the matching list (41). The emotional code matching module (43) simply compares the emotional code input to the module with those from the databases, and output a list of database entities that matches the input.

When emotional codes are assigned to all entities, many existing applications can be enhanced and new applications can be enabled—for example, commerce can find consumers, consumers can find consumers and consumers can find commerce. In one specific embodiment, the emotional code is displayed on an Internet search engine homepages and on consumer product and service websites. Consumers use the emotional code as a mean of filtering their web search according to their taste or style preferences. As a specific example, if a consumer is searching for shoes, he can click on an image corresponding to his personal emotional code and then enter 'shoes' on the search bar. The search engine then finds the shoes that suites the consumer's emotional preferences. In another example, an Internet auction site can facilitate a seller to specify the emotional code of the potential buyer of his product; and the buyer specifies his emotional code so as to narrow down the search.

In another preferred embodiment, the user's personal emotional code can be stored in a token under his possession. The token can be a credit card, a debit card, a smart card, the SIM (Subscriber Identity Module) card or USIM (Universal Subscriber Identity Module) card of a mobile phone; or any memory devices that can store data persistently. The user can occasionally synchronize the content of his token with information in the computerized emotional profiling server (35) so as to ensure data integrity and consistency.

When the user is shopping, his token can review his personal emotional code to the shop keeper so that the latter can select products that best match the user's emotional profile. In another embodiment, when the user enters a shopping mall, and he chooses to reveal his personal emotional code to others, he may receive up-to-date promotional offerings that match his personal emotional code from the shops in the mall. Alternatively, he can set up his token with requests for clothing or food, and his token can negotiate with the object emotional codes of merchants in his vicinity and alerts him when he is close by to a shop or restaurant that suits him.

Another application enabled by this invention is to use the emotional profile matching system (39) to find friends with similar or complimentary emotional preferences. This can simply be done by matching the personal emotional code of one user with those in the personal emotional database (106). The system will then report a list of individuals whose emotional preferences are similar to the user.

This invention can also enhance the existing Internet property matching sites so that home buyers can express his or her emotional preferences of the property that he wants to buy. The buyer specifies the emotional code of the property that he is interested in. Likewise, the seller states a similar emotional code for his property, and the emotional profile matching system (39) can then be used to match the buyers with the sellers. Although property matching is used as an example here, it is obvious that the same concept can be extended to other commercial applications such as vehicle purchasing, hotel booking, etc., and any applications that match one entity with another.

In yet another application enabled by this invention, the popular text-based quizzes can be replaced by quizzes in the visual imagery space. As a specific example, images are posted as questions, players also respond by select images in answering.

These are only some applications that can be enabled or enhanced using the inventive ideas described here. Those skilled in the art can apply these ideas to many other application domains.

Hardware and Software Implementation Details

Figure 14:
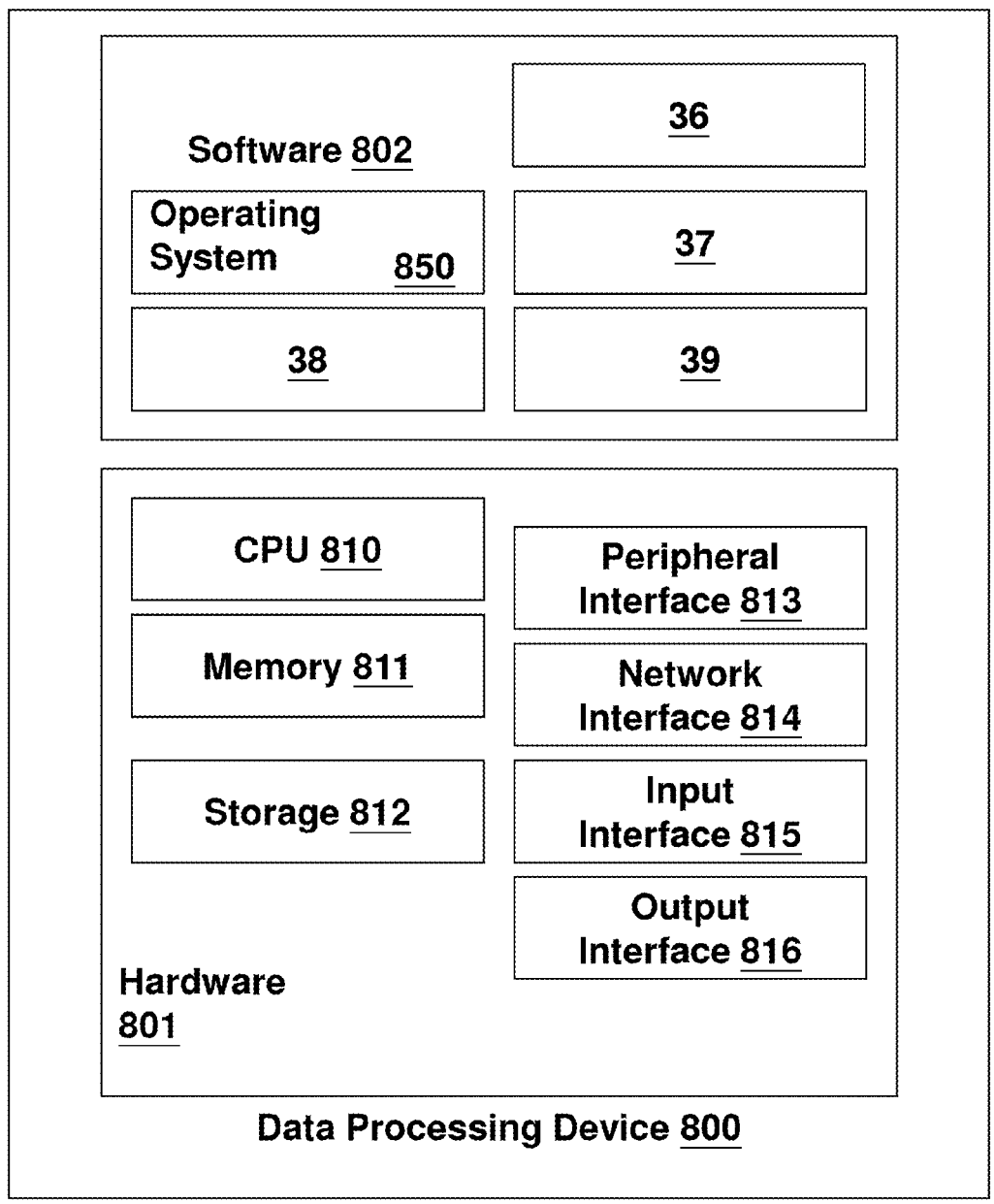
FIG. 14 shows the components of the data processing device.

FIG. 14 shows an exemplary data processing device 800 consisting of both the hardware 801 and software components 802 that can be used to implement the embodiment of the present invention. The hardware components in the present embodiment further comprises a Central Processing Unit (CPU) 810, memory 811, storage 812, and multiple interfaces such as the peripheral interface 813, network interface 814, input interface 815 and output interface 816.

CPU 810 can be a single microprocessor or multiple processors combined together. Memory 811 can include read-only memory, random-access memory or other memory technologies, singly or jointly combined. Storage 812 typically includes persistence storage such as magnetic hard disk, floppy disk, optical storage devices such as CD-ROM, and semiconductor storage devices such as flash memory cards, or other storage technologies, singly or in combination.

Input interface 815 is the interfacing components that connect the data processing device 800 to data inputting devices such as keyboard, keypad, pen-based device, mouse or other point devices, voice-input apparatus, scanner or other input technologies. Output interface 816 is the interfacing components for the data processing device 800 to send data to outputting devices such as CRT or flat panel display monitor, printer, voice output apparatus, laud speaker or other output technologies. Peripheral interface 813 may typically include the serial or parallel interface and the USB (Universal Serial Bus) interfaces, and other interfacing technologies. Network interface 814 enables the data processing device 800 to exchange information with the external data communication network such as the Personal Area Network (PAN), the Local Area Network (LAN), the Wide Area Network (WAN), the Internet, and other data communication network architectures. The network interface 814 can include the Ethernet interface, the Wireless LAN interface device, the Bluetooth interfacing device and other networking devices, singly or in combination.

Software 802 further includes the operating system 850, and the four application software systems as shown in FIG. 1. Operating system 850 is to manage all the hardware resources, and schedule executing priorities for all tasks and processes so that the four application software systems can all be executed in an orderly manner.

It should be understood for those skilled in the art that the division between hardware and software is a conceptual division for ease of understanding and is somewhat arbitrary. Moreover, it will be appreciated that peripheral devices in one computer installation may be integrated to the host computer in another. Furthermore, the application software systems may be executed in a distributed computing environment. The software program and its related databases can be stored in a separate file server or database server and are transferred to the local host for execution. The data processing device 800 as shown in FIG. 14 is therefore an exemplary embodiment of how the present invention can be implemented. Those skilled in the art will appreciate that alternative embodiments can be adopted to implement the present invention.

The preferred embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. An emotional profiling server comprising
a non-transitory computer-readable storage medium encoded with databases and modules configured to cause a Central Processor Unit (CPU) to execute predetermined steps, wherein said databases and modules further comprise:
  a) a media survey module configured to deliver at least one multi-media survey form to a plurality of users and to collect at least one answer from each user; said answer reflecting the emotional reflex of the user;
  b) a survey result database to store a plurality of survey results, each of said survey result comprising said at least one answer;
  c) a cluster analysis module configured to perform cluster analysis on said survey result database and produce at least one cluster;
  d) an emotional profile database that stores at least one emotional profile record
  wherein said media survey module collects and aggregates a plurality of answers from a plurality of users and stores said answers as survey results to said survey result database;
  wherein said cluster analysis module: i) performs cluster analysis on said aggregated answer to segregate said plurality of users into clusters, each cluster being a user segment, ii assigns an emotional code to said cluster, and iii)) stores said emotional code and other relevant cluster information as an emotional profile record in said emotional profile database.

2. The server according to claim 1 wherein said media survey module is further configured to communicate with said user via a computing device connected to a data communication network; said computing device is a desk-top computer, a portable computer, an information kiosk, a wireless mobile phone device, an interactive TV or an Internet TV; said data communication network is a local area network, a wireless network, the Internet, or any combination thereof.

3. The server according to claim 1 wherein databases and modules are configured to operate in a distributed computing platform such that said media survey module is configured to run on a first computer and to store said survey result to said survey result database in a second computer; said first and second computers being connected by a data communication network.

4. The server according to claim 1 wherein said multi-media object further comprises non-textual objects, check boxes, radio buttons or any combination thereof; said non-textual objects comprising images, photographs, video clips, audio files, or any combination thereof.

5. The server according to claim 1, wherein said databases and modules further comprise a personal emotional code database, said personal emotional code database configured for storing a plurality of the personal emotional codes for a plurality of users; each said personal emotional code corresponding to the emotional code assigned to the cluster to which said user belongs.

6. The server according to claim 5 wherein the personal emotional code of a specific user is stored in a non-volatile storage device under said specific user's possession, and said non-volatile storage device is a credit card, a debit card, a smart card, an identity card, a Subscriber Identification Module (SIM) card, or a Universal Subscriber Identification Module (USIM) card.

7. The server according to claim 5, wherein said databases and modules further comprise an object emotional code database, said object emotional code database storing the object emotional code of an object; said object emotional code is created by the steps of:
   i) assembling a user community of said object according to predetermined criteria;
   ii) obtaining said personal emotional code of each said user in said user community;
   iii) adding the number of users in said user community belonging to said personal emotional code;
   iv) identifying said personal emotional code that has the highest number of users; and
   v) assigning said personal emotional code as said object emotional code.

8. The server according to claim 7, wherein said databases and modules further comprise an emotional code matching module, said emotional code matching module is configured to perform the steps of comparing an emotional code of a first entity with an emotional code of a second entity and computing a matching score between said first entity and said second entity, wherein said first entity is a user or an object and said second entity is a user or an object.

9. A method for emotional profiling performed by an emotional profiling server comprising:
   a) delivering at least one multi-media survey form to a plurality of users;
   b) obtaining at least one answer to said survey form from each user; said answer reflecting the emotional reflex of the user;
   c) aggregating a plurality of answers obtained from a plurality of users;
   d) performing cluster analysis on said aggregated answers to segregate said plurality of users into at least one cluster, each cluster being a user segment comprising at least one user; and
   e) assigning an emotional code to each cluster.

10. The method according to claim 9 further comprising the step of assigning a personal emotional code to each said user, said personal emotional code corresponding to the emotional code assigned to the cluster to which said user belongs.

11. The method according to claim 10 further comprising the step of assigning an object emotional code to an object comprising:
   i) assembling a user community of said object according to predetermined criteria;
   ii) obtaining said personal emotional code of each said user in said user community;
   iii) adding the number of users in said user community belonging to said personal emotional code;
   iv) identifying said personal emotional code that has the highest number of users; and
   v) assigning said personal emotional code as said object emotional code.

12. The method according to claim 9 further comprising the steps of:
   i) identifying a user segment;
   ii) performing a second cluster analysis on a second emotional survey to obtain at least one sub-cluster; and
   iii) assigning an sub-emotional code to said sub-cluster.

13. The method according to claim 9 wherein said delivering step further comprises the step of obtaining a question and a plurality of multi-media objects to compose said multi-media survey form; said question and said plurality of multi-media objects retrieved from a multi-media database.

14. The method according to claim 9 further comprising the step of preferential questioning comprising the steps of:
   i) analyzing said answer in step (b);
   ii) composing a second survey form based on the result of said analyzing step by retrieving a question and a plurality of multi-media objects from a multi-media database; and
   iii) repeating step (b) to obtain additional answers from said user
   whereby further emotional reflexes of said user may be collected and analyzed.

15. The method according to claim 9 wherein said obtaining step further comprises the step of recording the time it takes for said user to answer.

16. The method according to claim 9 wherein said obtaining step further comprises the step of recording the sequential ordering of answers said user makes when said user selects more than one answer in said survey form.

17. The method according to claim 9 further comprising the step of comparing an emotional code of a first entity with an emotional code of a second entity and computing a matching score between said first entity and said second entity, wherein said first entity is a user or an object and said second entity is a user or an object.

18. A method of matching the emotional profile of a new user against at least one existing user in a survey result database performed by an emotional profiling server comprising the steps of:
   a) selecting an emotional survey document; said emotional survey document being designed for a specific domain and comprising at least one survey form;
   b) sending said survey form to said new user, said survey form further comprising at least one question and a choice of a plurality of multi-media objects;
   c) prompting said new user to choose at least one choice from said plurality of multi-media objects according to the emotional reflex response of said new user;
   d) collecting said at least one choice from said new user as survey result;

e) repeating steps (b), (c) and (d) for all survey forms in said emotional survey document;
f) matching said survey result against at least one survey result record retrieved from said survey result database and computing a matching score; said survey result record further comprising survey results from said existing user, answering same emotional survey document;
g) comparing said matching score with a pre-defined criterion; and
h) identifying said new user to said at least one existing user whose matching score satisfies said pre-defined criterion.

19. The method according to claim 18 wherein
i) said matching step further comprising computing a plurality of matching scores for a plurality of survey result records in said survey result database; storing said plurality of matching scores to a matching list and sorting said matching list in descending order;
ii) said comparing and identifying steps are replaced by the step of identifying at least one said existing user whose corresponding matching score is within the top-N entries in said matching list wherein N is a numerical integer between one and the size of said matching list and is specified by a designer.

20. The method according to claim 18 wherein said matching step further comprises the steps of:
i) identifying an existing choice by said existing user in said survey form for said at least one survey result records;
ii) incrementing said matching score by one if said choice from said new user in said survey form is the same as said existing choice in step (i); and
iii) repeating steps (i) and (ii) until all survey results are processed.

21. A method of identifying emotional profile of a new user performed by an emotional profiling server comprising the steps of:
a) Selecting an emotional survey document, said emotional survey document comprising at least one survey form;
b) sending said survey form to said new user; said survey form further comprising at least one question, a plurality of multi-media objects, and a plurality of choices, each said choice corresponding to said multi-media object;
c) prompting said new user to choose at least one choice from said plurality of multi-media objects according to the emotional reflex response of said new user;
d) collecting said at least one choice from said new user as survey result;
e) repeating steps (b), (c) and (d) for all survey forms in said emotional survey document;
f) computing at least one matching score using said survey result and at least one emotional profile record retrieved from an emotional profile database; said emotional profile record being created by clustering a plurality of previous obtained survey results obtained from at least one existing user; further comprising an emotional code, and cluster statistics associated with said emotional code;
g) comparing said matching score with a pre-defined criterion; and
h) assigning said new user to said emotional code in said emotional profile record whose match score satisfies said pre-defined criterion.

* * * * *